United States Patent [19]

Jassawalla et al.

[11] 4,142,524
[45] Mar. 6, 1979

[54] CASSETTE FOR INTRAVENOUS DELIVERY SYSTEM

[75] Inventors: Jal S. Jassawalla, San Francisco; Herbert Chen, Berkeley; Ingvar Olaffson, Albany, all of Calif.

[73] Assignee: Andros Incorporated, Berkeley, Calif.

[21] Appl. No.: 802,679

[22] Filed: Jun. 2, 1977

[51] Int. Cl.² .............................................. A61M 5/00
[52] U.S. Cl. ................................. 128/214 F; 417/435; 128/DIG. 12
[58] Field of Search ........... 128/214 R, 214 C, 214 F, 128/214 E, 214.2, DIG. 12, 274; 417/435

[56] References Cited

U.S. PATENT DOCUMENTS

| 2,954,738 | 10/1960 | DiVette | 128/214 R X |
| 3,559,644 | 2/1971 | Staft et al. | 128/274 X |
| 3,874,826 | 4/1975 | Lundquist | 128/214 F X |

FOREIGN PATENT DOCUMENTS 2316509  1/1977  France ................... 128/214 F

Primary Examiner—Dalton L. Truluck
Attorney, Agent, or Firm—Fitch, Even, Tabin & Luedeka

[57] ABSTRACT

A cassette is described for use in an intravenous delivery system having a pump. The volume of a main chamber defined by the cassette body is varied by a membrane in a wall thereof while unidirectional inlet and outlet valves maintain the direction of fluid flow into and out of the main chamber. A prechamber is positioned above the inlet port in order to accumulate air from the upstream portion of the intravenous delivery system in which the cassette is used.

2 Claims, 2 Drawing Figures

U.S. Patent
Mar. 6, 1979
4,142,524
FIGURE 1.
FIGURE 2.
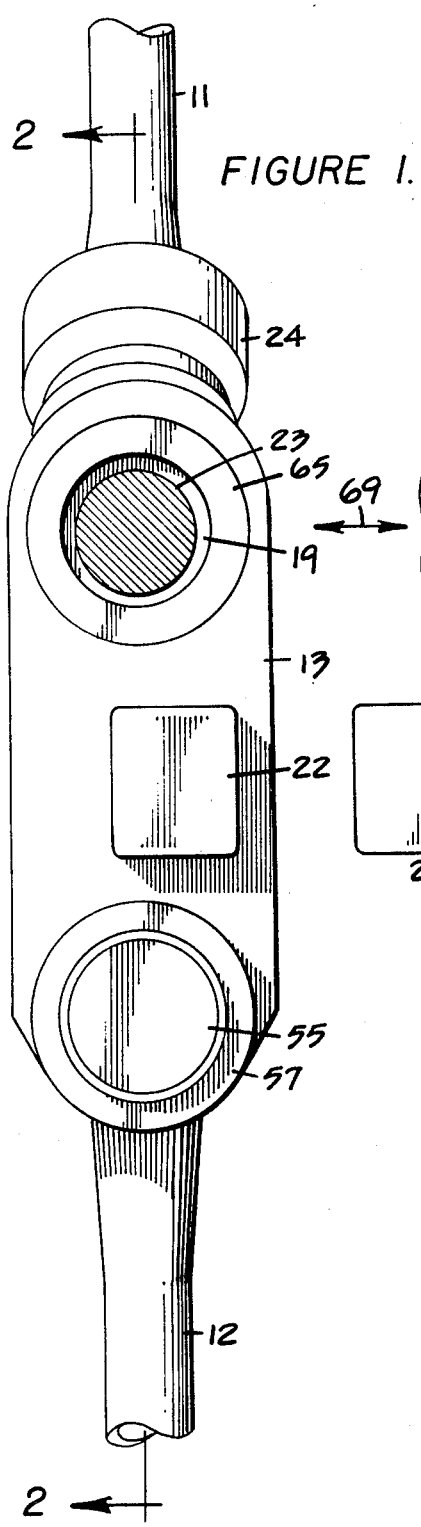
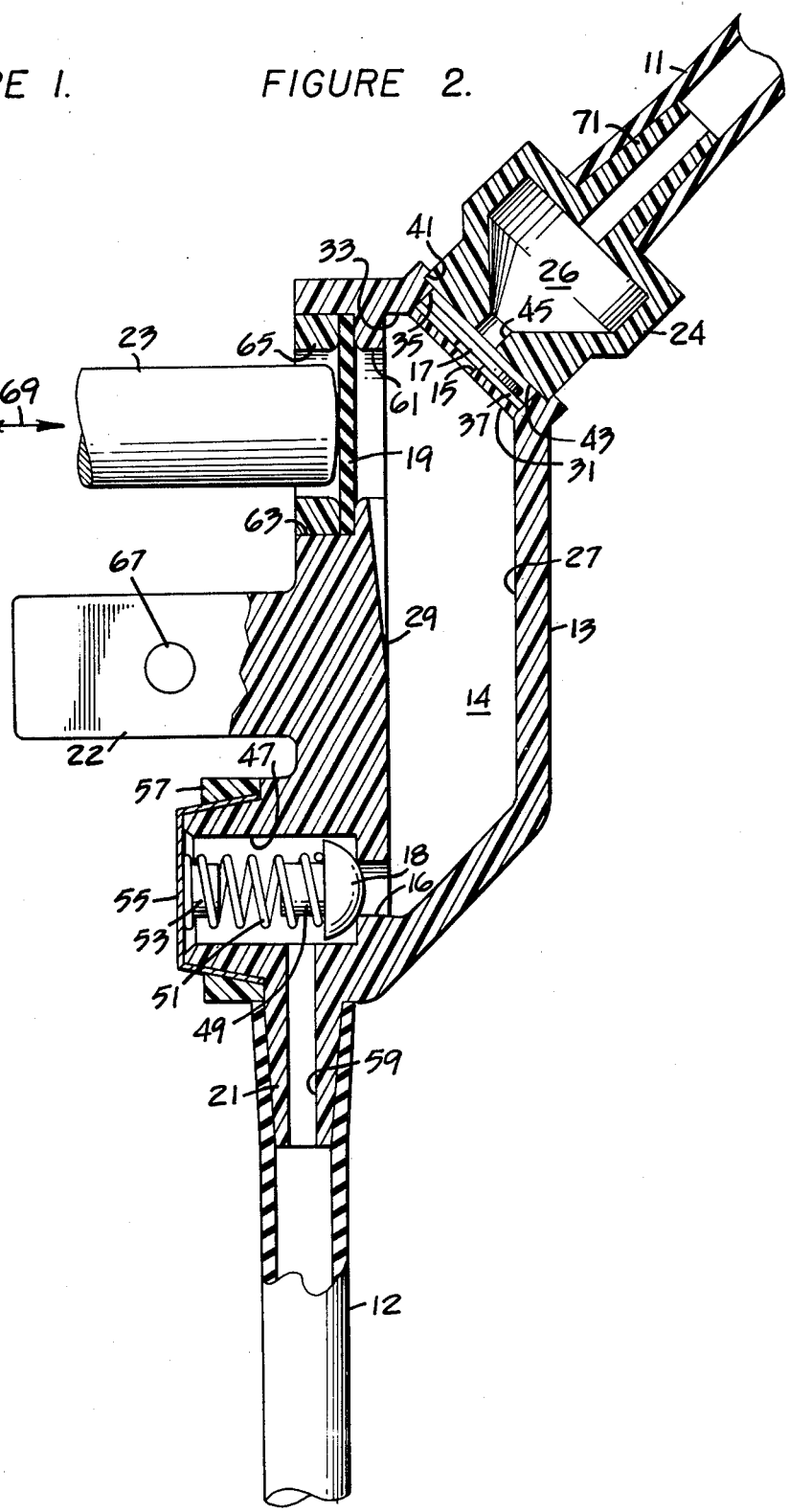

CASSETTE FOR INTRAVENOUS DELIVERY SYSTEM

The present invention relates to the field of medical fluid delivery systems and, more particularly, to intravenous delivery systems for the delivery of drugs, plasma, glucose solutions and the like.

Various systems for the delivery of fluids intravenously or intra arterially are well known in the prior art, and such systems are in widespread daily use in hospitals throughout the world. These systems (I.V. systems) are commonly used for the intravenous or intra arterial delivery of fluids such as glucose solutions and blood plasma as well as for the delivery of drugs, all at controlled delivery rates depending on the patient's needs and, in the case of drugs, the drug concentration being delivered.

The oldest and most commonly used form of delivery system comprises a fluid container, a drip chamber and an adjustable clamp in the tube leading from the drip chamber to the needle penetrating the vein. The fluid container or bottle is supported at an elevated position with respect to the patient, with the drip chamber typically arranged immediately thereunder. Transparent walls in the drip chamber coupled with a fixed volume of air therein allows the visual determination of the drip rate, which in turn is adjustable by the hose clamp. Thus, as fluid being delivered seeps past the pinched area of the hose, the air pressure in the drip chamber decreases, thereby encouraging the formation and dislodging of a drop from the tip of the small tube into the drip chamber coupled to the bottle. Such systems may be used alone or in conjunction with metering or pumping mechanisms with the visually observed drip rate being used as a cross-check to verify the proper operation of the pumping device.

Another type of I.V. system which has come into substantial use in recent years employs what is commonly referred to as some form of a peristaltic pump. Such pumps are characterized by a length of flexible tubing which is disposed within an arc between a stator-like member and a rotor assembly. The rotor assembly is provided with a plurality of rollers which, upon rotation of the rotor assembly, successively pinch-off the tube and advance the location of the pinch-off so as to progressively advance the fluid through the tube at a rate determined by the rate of rotation of the rotor.

Typically such systems are driven in rotation by some form of motor-gear assembly capable of rotating the rotor at low speeds so as to provide the generally desired low pumping rate. These pumps commonly have a disposable element in the fluid flow path so that the length of tubing in the pump may be replaced after each use.

In principle, the further advantage of low and variable flow rates is possible through use of a positive displacement pump. In practice, however, these systems characteristically exhibit poor accuracy and poor reproducibility. They also have the disadvantages of being able to pump air or both air and liquid continuously against a rather substantial back pressure. They are mechanically complex, and require a substantial amount of power, thereby making them relatively expensive and difficult to use on battery operation.

Another form of pump is the positive displacement pump of U.S. Pat. No. 3,620,650. The pumps disclosed therein have some advantages over the previously described pumps in that they are specifically configured so as to not pump air, thereby providing for automatic shut-off of the pump in the event of exhaustion of the supply of fluid being injected. Also, the pump uses a form of electromagnetic device including a pluse source providing a variable pulse rate to thereby vary the pump rate.

The pumps disclosed in the above patent, however, have a number of disadvantages in comparison to the present invention. In particular, the pump of FIG. 4 of U.S. Pat. No. 3,620,650 is a relatively expensive pump which must be fabricated from a relatively large number of close tolerance parts. Aside from the need for the coil springs and a close fitting piston, the pump requires a magnetic member within the fluid chamber which in itself has certain disadvantages. Obviously, the magnetic member must be a metal member and accordingly, must be suitably protected against corrosion, etching, and other adverse effects caused by any of the wide range of fluids which might be injected.

Even if it were used as a disposable pump so that deterioration of the pump would not be cumulative, all deterioration of pump parts must be avoided because of possible adverse effects of any dissolved materials. Also, since the magnetic member is within the fluid chamber whereas the actuating coil is external to the enclosure, considerable electrical power is required to actuate the solenoid, thereby making battery operation very difficult.

Another positive displacement pump is shown in U.S. Pat. No. 3,874,826. This pump is also relatively mechanically complex and, like the pump of U.S. Pat. No. 3,620,650, not ideally suited for disposable use because of its complexity and apparent high cost. For example, because the pump employs a piston protruding a substantial distance into the pumping chamber, a germ barrier sleeve must be employed. Severe problems of fit and friction induced wear inherently result from such a construction.

An improved form of positive displacement pump is shown and described in copending U.S. patent application Ser. No. 701,238, filed June 30, 1976 and entitled "Intravenous and Intra Arterial Delivery System". That application is assigned to the assignee of the present invention. The system described in the above patent application includes a pump and detachable cassette used in connection therewith. The cassette has a pumping chamber, the volume of which is varied by the pump. Inlet and outlet valves cause the intravenous fluid to enter and leave the chamber of the cassette while at the same time ensuring that air is not pumped.

The present invention relates to an improved cassette design for use in a system of the general type described in the aforesaid patent application.

It is accordingly an object of the present invention to provide an improved intravenous delivery system.

Another object of the invention is to provide a low cost disposable cassette for use in an intravenous delivery system and which connects the pump therein.

A further object of the invention is to provide a disposable cassette for use in an intravenous delivery system wherein air is prevented from entering the pumping chamber.

Intravenous delivery systems of the type described above in connection with the prior art suffer from one inherent disadvantage. Although air entering the main chamber or pumping chamber of the cassette is substantially prevented from passing downstream in the intravenous delivery system, nevertheless it can have a deleterious effect on the operation of the system. This is because accumulated air in the cassette main chamber causes the pumping rate to decrease proportionally. Minor variations in the pumping rate are in most cases tolerable. Nevertheless, some intolerable variation in pumping rate may occur and may be extremely difficult to detect.

It is therefore a more specific object of the invention to avoid this previously inherent disadvantage.

Additional objects and advantages of the invention will be apparent from the following description having reference to the accompanying drawings.

In the drawings:

FIG. 1 is a side view of a cassette for an intravenous delivery system in accordance with the present invention.

FIG. 2 is a view, with parts shown in section, taken along section line 2—2 of FIG. 1.

Very generally, the cassette of the invention operates between an upstream portion or conduit 11 and a dowstream portion or conduit 12 of the intravenous delivery system in which the cassette is employed. The cassette includes a cassette body 13 having a main chamber 14, an inlet port 15 and an outlet port 16. First valve means 17 are coupled to said inlet port for allowing unidirectional flow into said main chamber 14 through the inlet port 15. Second valve means 18 are coupled to the outlet port for allowing unidirectional flow out of the main chamber through the outlet port. Movable means such as the diaphragm 19 vary the volume of the main chamber. Collector means 21 are provided at the outlet port for directing fluid from the outlet port toward a needle. Coupling means 22 are provided for coupling the cassette body 13 to a pump assembly, a pump element 23 of the pump assembly (not otherwise shown) engaging the movable means or diaphragm 19. Means 24 define a prechamber positioned above the inlet port and communicating therewith. The prechamber 26 has a volume selected to accumulate air from the upstream portion of the intravenous delivery system in an amount sufficient to maintain the chamber air free.

Referring in greater detail to the drawings, the cassette body 13 is of generally elongated oval outline as viewed in FIG. 1, having semicircular end configurations. The internal surfaces of the casette body facing on the chamber 14 are of similar outline with one of the surfaces 27 being smaller in the area enclosed by the outline than the other of the surfaces 29. The surfaces 27 and 29 lie in parallel planes, and are joined by a slanted wall 31 having a step 33 at one edge perpendicular to the surface 29.

The inlet port 15 intersects the slanted surface 31 adjacent the upper end of the chamber 14 as viewed in FIG. 2. A circular recess 34 is provided in the cassette body coaxial with the opening or inlet port 15. A plurality of ribs 37 are formed in the bottom surface of the recess 35 extending inwardly from the periphery thereof to adjacent the opening or inlet port 15.

The valve means 17 comprise a disc which rests against the ribs 37, the disc being of smaller diameter than the diameter of the recess 35. The prechamber defining means 24 are secured in an annular recess 41 coaxial with the recess 35. The prechamber defining means have a surface 43 facing on the recess 35 to form a valve chamber in which the disc 17 is movable between a position resting against the ribs 37 and a position resting flush against the surface 43. When the pressure inside the chamber 14 exceeds the pressure on the opposite side of the disc, the disc is pressed against the surface 43, thereby closing off the opening 45 which passes through the prechamber defining means 24 from the prechamber 26. When the pressure in the chamber 14 is lower than the pressure on the opposite side of the disc 17, the disc moves against the ribs 37, allowing flow around periphery of the disc, between the ribs, and through the inlet port 15. Thus, the valve means 17 operate to provide unidirectional flow into the chamber 14 and to prevent backflow out of the chamber 14.

At the opposite end of the elongated main chamber 14, the outlet valve means 18 are positioned. The outlet valve means 18 are positioned in a generally cylindrical recess 47 formed in the cassette body coaxially of the outlet port 16. The valve means 18 include a button head which abuts the outlet port 16, and a valve stem 49 extending therefrom. A coil spring 51 is joined to the valve stem 49 and extends axially thereof within the chamber 47. The opposite end of the coil spring 51 is secured to a stem 53 which, in turn, is secured to a membrane 55. The membrance 55 is stretched over the opening of the recess 47 and is held in place by a clamping ring 57. When the cassette is mounted to the pump, suitable means, not shown, press against the membrane 55 and bias the button head of the valve means 18 against the outlet port 16 to close the outlet port. Sufficient pressure within the chamber 14, however, depresses the coil spring 51 and allows fluid flow past the valve means 18 and into the chamber 47.

The collector means 21, in the form of a nipple, include a passage 59 which communicates with the chamber 47. Fluid can then flow through the passage 59 and into the downstream portion of the intravenous delivery system, illustrated by the tube 12.

The movable means 19 which are provided for varying the volume of the chamber 14, in the illustrated embodiment, comprise a membrane stretched across an opening 61 in the cassette body 13. The membrane 19 spans the opening 61 and the periphery thereof extends into a recess 63 of larger diameter. A clamping ring 65 seals the periphery of the membrane in the recess.

With the cassette removed from the pump, the outlet valve 18 is not sealed against the outlet port 16. In this position fluid can flow through the inlet port 15 and the outlet port, and the cassette can be primed by holding it vertical in the inverted position with the outlet valve on top.

As indicated above, the coupling means 22 are provided to secure the cassette in the proper position with respect to the pump assembly. The coupling means in the illustrated embodiment comprise a tongue which extends into a suitable recess, not shown, on the pump. A detent 67 is provided on the pump to be engaged by a suitable spring bias plug to thus secure the cassette in position. The illustrated portion of the pump comprises the rod or pump element 23 which reciprocates in the direction of the arrow 69 and which has a rounded end engaging the membrane 19. Ideally, the membrane is biased slightly inwardly at all times by the pump rod so that the amount of reciprocation of the rod accurately governs and is proportional to variation of the volume of the chamber 14.

In operating the illustrated cassette, movement of the rod 23 to the right in FIG. 2 causes a diminution in the total volume of the chamber 14. This increases the pressure therein, biasing the disc 17 against the surface 43 to close the inlet port while at the same time urging the valve 18 away from its position against the outlet port 16. Thus, fluid is allowed to flow through the outlet port into the chamber 47 and then through the passage 59 to the downstream portion 12 of the intravenous delivery system.

When the rod 23 moves to the left from the previously described position, the volume of the chamber 14 enlarges, thus reducing the pressure therein. This causes the valve means 18 to seal the outlet port 16 while at the same time allowing the disc 17 to seat against the ribs 37. Thus, fluid can flow through the inlet port 15.

Although a significant advantage of the foregoing described cassette lies in its inability to pump air, thus preventing air from entering the downstream portion 12 of the intravenous delivery system, air can still have a deleterious effect on the operation of the system. This is because any air entering the chamber 14 results in a decrease in the flow rate which can be of such significance as to be a problem. Such a decrease in the flow rate may go undetected for sufficiently long periods of time as to cause serious problems.

The prechamber defining means 24 are provided to prevent air from entering the main chamber 14 of the cassette. The prechamber 26 defined thereby is positioned above the inlet port 15 communicating therewith. A nipple 71 extends from the prechamber defining means 24 in axial alignment with the opening 45 and the inlet port 15. The upstream portion 11 of the intravenous delivery system, shown by a portion of a tube, is coupled to the nipple 71.

Air is frequently present in the upstream portion of a typical intravenous delivery system. Bubbles of air commonly adhere to the sides of the tubing and other passages with a tendency to agglomerate, thus migrating toward the cassette. Air may also enter the upstream portion of the intravenous delivery system through injection septums or slow leaks, particularly between the tubing and the drip chamber, not shown, commonly employed in intravenous delivery systems. The prechamber 26 effectively traps the air thus preventing it from entering the chamber 14. The volume of the prechamber 26 is selected depending upon the expected volume of air normally working its way down toward the cassette during the course of an intravenous delivery. Thus, the volume of the prechamber 26 must be significant and the prechamber must be located at a level higher than the inlet port. Where the volume of the chamber 14 is of the order of three to four cubic centimeters, the volume of the prechamber 26 may be of the order of one-half cubic centimeter. The preferred range for the volume of the prechamber is from about 10% to about 20% of that of the main cassette chamber.

In the event that the prechamber 26 fills completely with air, air may then flow into the chamber 14. As previously mentioned, because of the compressibility of air, the cassette is unable to pump air but nevertheless will exhibit a lowering of the pumping rate of the fluid. For this extreme condition, the flow rate observable in the drip chamber, not illustrated but normally present in an intravenous delivery system, will readily be perceived to be less than that desirable. This is because any amount of air entering the system sufficient to fill the prechamber 26 during the expected intravenous delivery period will result from a leak of such significance as to be readily perceived.

It may be seen, therefore, that the invention provides an improved cassette for use in an intravenous delivery system. The cassette is of simple construction, and low in cost and effectively prevents air from entering the main chamber of the cassette, thus ensuring a constant and accurate rate of delivery of the intravenous fluid.

Various modifications of the invention in addition to those shown and described herein will become apparent to those skilled in the art from the foregoing description and accompanying drawings. Such modifications are intended to fall within the scope of the appended claims.

What is claimed is:

1. A cassette for use in an intravenous delivery system of the limited positive displacement type having a reciprocatory pump member, said cassette operating between an upstream portion and a downstream portion of the intravenous delivery system and comprising, a generally elongated cassette body having opposite walls of oval outline having semicircular end configurations, said body defining an elongated main chamber with opposite parallel surfaces of substantially the same outline but of different sizes and with a slanted wall joining said surfaces, said cassette body defining an inlet port to said main chamber proximate one end thereof and passing through said slanted wall, one of said opposite walls defining the larger of said opposite parallel surfaces of said main chamber and having first and second openings therein spaced toward opposite ends thereof, respectively, each of said openings being of substantially smaller area than the area of said larger parallel surface, a membrane spanning said first opening adapted for engaging the reciprocatory pump member for varying the volume of said main chamber in response to movement of said reciprocating pump member, said second opening forming an outlet port arranged proximate the other end of said main chamber from said inlet port, a tongue extending from said elongated wall of said cassette body, said tongue having detent means thereon for coupling said cassette to a pump assembly having a pump element engageable with said membrane, said cassette body having further wall means defining a prechamber arranged above and in communication with said inlet port and extending from said slanted wall, said prechamber having a volume selected to accumulate air from the upstream portion of the intravenous delivery system in an amount sufficient to maintain said main chamber substantially free of air.

2. A cassette according to claim 1 wherein said prechamber defining means include means for coupling said prechamber to the upstream portion of the delivery system.

* * * * *